United States Patent [19]

Rajaiah et al.

[11] Patent Number: 5,304,616
[45] Date of Patent: Apr. 19, 1994

[54] DENTURE STABILIZING COMPOSITIONS HAVING IMPROVED HOLD

[75] Inventors: Jayanth Rajaiah, Bridgeport; Abel Saud, Milford, both of Conn.; Bruce J. MacKay, Guilford, Conn.

[73] Assignee: The Procter & Gamble Company, Cincinnati, Ohio

[21] Appl. No.: 966,120

[22] Filed: Oct. 22, 1992

Related U.S. Application Data

[63] Continuation of Ser. No. 712,831, Jun. 10, 1991, abandoned.

[51] Int. Cl.$^5$ .......................... C08F 30/04; C08F 8/44
[52] U.S. Cl. .................. 526/240; 525/327.8; 523/118; 523/120
[58] Field of Search ............. 525/327.8, 327.9; 526/240; 523/118, 120

[56] References Cited

U.S. PATENT DOCUMENTS

| | | | |
|---|---|---|---|
| 3,003,988 | 10/1961 | Germann et al. | 260/33.6 |
| 4,223,109 | 9/1980 | Wolgemuth | 525/327 |
| 4,569,955 | 2/1986 | Dhabhar | 523/120 |
| 4,758,630 | 7/1988 | Shah et al. | 525/207 |
| 4,910,247 | 3/1990 | Haldar et al. | 524/400 |
| 4,980,391 | 12/1990 | Kumar et al. | 524/45 |
| 5,073,604 | 12/1991 | Holeva et al. | 525/327 |

*Primary Examiner*—Paul R. Michl
*Assistant Examiner*—Lavonda DeWitt
*Attorney, Agent, or Firm*—David K. Dabbiere; Kathleen M. Harleston; Douglas C. Mohl

[57] ABSTRACT

Disclosed are stabilizer compositions comprising specific mixed partial salts of a lower alkyl vinyl ether-maleic acid copolymer wherein said partial salts containing from about 15% to about 40% free acid, and as the cationic salt function:

(a) from about 0.1% to about 80% strontium cations; and (b) from about 0.1% to about 65% zinc cations of the total initial carboxyl groups reacted. Also disclosed are denture stabilizing compositions comprising these mixed partial salts, as well as denture stabilizing compositions comprising a safe and adhesively effective amount of two or more denture adhesive components wherein one of said denture adhesive components is the mixed partial salt(s) of the present invention.

18 Claims, No Drawings

DENTURE STABILIZING COMPOSITIONS HAVING IMPROVED HOLD

This is a continuation of application Ser. No. 712,831, filed Jun. 10, 1991 now abandoned.

TECHNICAL FIELD

This invention relates to improvements in adhesives, in particular, improved denture adhesives.

BACKGROUND OF THE INVENTION

Ordinary removable dentures, dental plates, and the like, comprise teeth mounted in a suitable plate or base. Dentures function as a substitute for missing teeth and serve as a replacement for all or a portion of the teeth ordinarily found in the oral cavity. Although dentures generally are skillfully prepared, often they do not fit perfectly. Moreover, no matter how satisfactory at first, after a period of time the fit of the denture becomes loose and imperfect due to natural shrinkage and changes in the gums, mucous tissues, and the like. Loose and imperfectly fitted dentures usually are corrected and stabilized by the use of a denture stabilizer. Denture stabilizers are used to fill the interstices between the dentures and the gums or tissues. Prior to placement of the denture in the oral cavity, a denture stabilizer is applied to the denture-plate surface which, for a perfect fit, should uniformly contact the gums and mucous tissues. The denture stabilizer is formulated not only for its adherent properties, but also to provide a cushion or gasket between the denture and the gums or tissues, thereby positioning the denture securely in the oral cavity.

Requirements and characteristics for a satisfactory denture stabilizing composition are many and are dictated by numerous factors. Desirably, one daily application of such a composition should function as an effective means for insulating, cushioning, and securely positioning the denture. The composition should retain its characteristics and properties in the typical powder and cream forms during storage under various climatic conditions such as high temperature and humidity; be readily and easily capable of application to the denture surface; not be irritating or uncomfortable to the user; be safe and nontoxic; have no disagreeable odor or color; have no unpalatable taste; optionally provide antiseptic and germicidal properties for preventing or inhibiting the growth of organisms ordinarily found in the mouth; and function as an agent for prevention of putrefaction or malodorous decomposition of foods or secretions lodging beneath of adjacent to the denture. The stabilizing material must be capable of imbibing water and saliva and swelling, so as to fill the interstices between the denture and the gum or mucous tissues. The stabilizer should not attack or damage the denture, as by causing a crazing of the denture-plate material. Additionally, the stabilizer should be stable to bacteria, molds and enzyme systems found in the oral cavity, and have a pH that is nonirritating to the oral mucosa, generally 5-8.5, preferably a pH around neutrality. The mechanical strength of the stabilizing mass, be it gel or colloid, formed by imbibition of water should be great enough to securely maintain the position of the denture under normal use, and not so great as to make denture removal difficult when desired, or as to damage or injure the gums, tissues or denture upon removal.

There has been a considerable effort made over many years to develop improved denture adhesives. Both synthetic and natural polymers and gums have been used singly, in combination, and in combination with various additives.

European Patent 64,672 to Dhabhar and Schmidt, published Nov. 17, 1982, relates to a hydrophilic denture adhesive containing an adhesive polymeric fraction comprising carboxymethylcellulose (CMC) and polyethylene oxide in a hydrophilic vehicle.

European Patent Application 140,486 to A. J. Desmaris, filed Jul. 31, 1984 relates to denture adhesive compositions containing a hydrophobically modified water-soluble polymer, alone or admixed with an alkali metal salt of CMC. Hydrophobically modified hydroxyalkyl celluloses and copolymers of ethylene oxide and long chain epoxy-alkanes are preferred for use in the compositions.

U.S. Pat. No. 4,280,936 to Dhabhar, Heyd and Schmidt, issued Jul. 28, 1981, relates to improved denture adhesives containing a specified ratio of CMC and polyethylene oxide in a mineral oil base.

U.S. Pat. No. 4,474,902 to Dhabhar and Schmidt, issued Oct. 2, 1984, relates to improved denture adhesives containing karaya gum in a hydrophilic vehicle. See also U.S. Pat. No. 4,514,528, issued Apr. 30, 1985, and U.S. Pat. No. 4,518,721, issued May 21, 1985 to these same inventors, relating, respectively, to improved denture adhesives containing adhesive polymeric fractions consisting of admixtures of partial salts of lower alkyl vinyl ether maleic anhydride-type copolymers with CMC or polyethylene oxide, as well as denture adhesives containing CMC and polyethylene oxide. See also U.S. Pat. No. 4,522,956, issued Jun. 11, 1985 to Dhabhar and Schmidt relating to improved denture adhesives containing polyethylene oxide as the sole adhesive component in a hydrophilic vehicle comprising certain polyethylene glycols.

Other denture adhesives are described in U.S. Pat. No. 4,530,942, issued Jul. 23, 1989; U.S. Pat. No. 4,542,168, issued Sep. 17, 1985; and U.S. Pat. No. 4,569,955, issued Feb. 11, 1986.

U.S. Pat. No. 4,529,748 to H. G. P. Wienecke, issued Jul. 16, 1985, relates to dental prosthesis adhesives formed from film-forming substances such as various cellulose derivatives, acrylate polymers, methacrylate polymers, and other film-providing substances.

U.S. Pat. No. 4,138,477 to Gaffar, issued Feb. 6, 1979 discloses oral compositions to control mouth odor containing zinc-polymer combinations formed from zinc reacted with an anionic polymer containing carboxylic, sulfonic and/or phosphonic acid radicals.

U.S. Pat. No. 3,003,988, to D. P. Germann et al., issued Oct. 10, 1961, describes certain water-sensitized, but water-insoluble, materials for stabilizing dentures which are synthetic, hydrophilic, colloidal materials comprising mixed partial salts and esters of lower alkyl (1 to 4 carbons) vinyl ether-maleic anhydride-type copolymers, said mixed partial salts and esters containing both divalent calcium and monovalent alkali (i.e., sodium, potassium and ammonium) cations.

U.S. Pat. No. 4,758,630 to Shah et al., issued Jul. 19, 1988 relates to zinc and strontium partial salts of lower alkyl ($C_1$ to $C_4$) vinyl ether-maleic acid copolymers, wherein said zinc and strontium cations are "unmixed" with any other cations or ester functions in the copolymeric salt, the remaining initial carboxyl groups being unreacted. These lower alkyl vinyl ether-maleic acid copolymers are referred to hereinafter by the abbreviated term "AVE/MA copolymer" and the methyl vinyl ether-maleic acid copolymer as "MVE/MA copolymer". Further, European Patent Application 396,411, to Holeva and Gounaris published Nov. 7, 1990, discloses mixed partial MVE/MA copolymer salts.

It is known, therefore, that combinations of mixed and unmixed partial salts of lower alkyl vinyl ether-maleic anhydride-type copolymers are useful as denture adhesive compositions.

Yet, the search continues for denture stabilizers that will provide the above-described characteristics and, importantly, will maintain the secure fit of the denture over prolonged periods (10-14 hours) without the need for reapplication.

In accordance with the present invention, improved adhesive and other characteristics are obtained in a denture stabilizing composition by using specific single mixed partial salt(s) of a lower alkyl vinyl ether-maleic acid copolymer.

It is an object of the present invention to provide improved denture stabilizers which are easy to manufacture and that will be stable over prolonged periods in the oral cavity, yet will allow easy removal of the denture on demand.

It is a further object of the present invention to provide denture compositions which provide the user with improved sensory, such as flavor, benefits.

It is a further object to provide such stabilizers using toxicologically-acceptable, palatable materials.

It is another object herein to provide stabilizers that perform well in the presence of moisture, particularly in the presence of body fluids such as saliva, perspiration and blood.

These and other objects are secured by the present invention, in the manner disclosed hereinafter.

SUMMARY OF THE INVENTION

The present invention encompasses stabilizer compositions comprising: the mixed partial salt of a lower alkyl vinyl ether-maleic acid copolymer consisting essentially of the repeated structural unit:

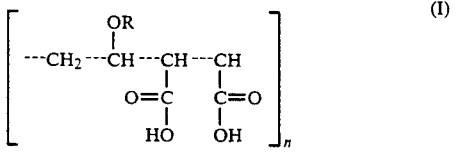

wherein R represents a $C_{1-4}$ alkyl radical, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salts containing from about 15% to about 40% free acid, and as the cationic salt function:

(a) from about 0.1% to about 80% strontium cations; and (b) from about 0.1% to about 65% zinc cations
of the total initial carboxyl groups reacted.

Also disclosed are denture stabilizing compositions comprising these mixed partial salts, as well as denture stabilizing compositions comprising a safe and adhesively effective amount of two or more denture adhesive components wherein one of said denture adhesive components is the mixed partial salt(s) of the present invention.

Preferably these mixed partial salts are used along with a water-sensitized polymeric material selected from the group consisting of natural gums, synthetic polymers, saccharide derivatives, cellulose derivatives, and mixtures thereof.

All percentages and ratios used herein relating to the neutralization of the salts of the present invention are based upon the stoichiometric percent of the cations present in the salt. All other percentages and ratios used herein are by weight, unless otherwise specified.

DETAILED DESCRIPTION OF THE INVENTION

The polymeric salts of the present invention are the mixed partial salt of a lower alkyl vinyl ether-maleic acid copolymer consisting essentially of the repeated structural unit:

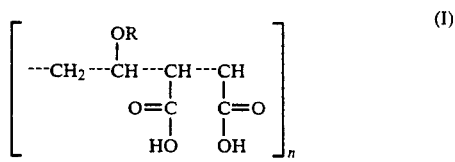

wherein R represents a $C_{1-4}$ alkyl radical, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salts containing from about 15% to about 40% free acid, and as the cationic salt function:

(a) from about 0.1% to about 80% strontium cations; and (b) from about 0.1% to about 65% zinc cations
of the total initial carboxyl groups reacted.

R is preferably methyl.

Preferably, these mixed partial salts comprise from about 20% to about 65%, more preferably from about 40% to about 65% strontium cations, and from about 1% to about 40%, more preferably from about 2% to about 20% zinc cations and from about 25% to about 35% free acid.

The mixed partial salts preferably further comprise from about 0.1% to about 10%, and more preferably from about 0.1% to about 5% iron cations. The mixed partial salts also preferably further comprise from about 0.1% to about 25%, and more preferably from about 0.1% to about 20% sodium cation.

The subject polymeric salts are advantageously prepared by the interaction of the AVE/MA copolymer (I) with cationic calcium, sodium, zinc, strontium and iron compounds having a functional group typical of reactants of carboxylic acid, such as, for example, the hydroxide, chloride, acetate, carbonate, halide, lactate, etc. in an aqueous medium. In a preferred embodiment, the carbonate of strontium, the oxide of zinc, chloride of iron and hydroxide of sodium are utilized: Since zinc hydroxide is not commercially available, its use as a reactant is readily and more economically accomplished by employing an aqueous slurry of particulate zinc oxide which, although practically insoluble in water, provides hydration to zinc hydroxide on the particulate surface. Aqueous solutions of strontium oxide, however, which form the hydroxide when treated with water (caution: heat evolution), may also be used.

Anions that form toxic, irritating or contaminating by-products should be avoided, or special precautions and treatment provided to assure the removal and absence of such by-products from the polymeric salt end-product. The particular compound used should be substantially pure to assure obtaining a substantially pure, substantially off-white polymeric salt end-product.

The lower alkyl vinyl ether maleic acid (AVE/MA) copolymers (I) are readily obtained by copolymerizing a lower alkyl vinyl ether monomer, such as methyl vinyl ether, ethyl vinyl ether, divinyl ether, propyl vinyl either and isobutyl vinyl ether, with maleic anhydride to yield the corresponding lower alkyl vinyl ether-maleic anhydride copolymer which is readily hydrolyzable to the acid copolymer (I). Both anhydride and acid forms are also available from commercial suppliers. For example, the GAF Corporation, Wayne, N.J., provides both the polymeric free acid form (I) and the corresponding anhydride form under its "GANTREZ" trademark as the "GANTREZ S Series" and "GANTREZ AN Series", respectively. In the former acid series, the GANTREZ S-97 (M.W.=50,000) is particularly suitable, and, in the latter anhydride series, the GANTREZ AN-149 (M.W.=50,000), the GANTREZ AN-169 (M.W.=67,000) and the GANTREZ AN-179 (M.W.=80,000) copolymers are particularly suitable. Said acid and anhydride forms of AVE/MA copolymers, having an average molecular weight of from about 50,000 to about 80,000 (as measured by membrane osmometry in 2-butanone 1–10 grams/1000 ml solution), are also characterized by having the previously described specific viscosity parameter of more than 1.2. When the anhydride copolymer dissolves in water, the anhydride linkage is cleaved so that the highly polar, polymeric free acid (1) is formed. Accordingly, the anhydride form, which is relatively less expensive than the acid form, may be used as a convenient and cheaper precursor for the acid. Elevated temperatures may be advantageously employed to enhance the rate of anhydride-to-acid hydrolysis.

In general, the lower alkyl vinyl ether-maleic acid copolymer (I), or its corresponding anhydride, is added to water preheated to about 70°-80° C. with vigorous stirring to form a homogeneous mixture. If the anhydride precursor is utilized, it is recommended that the aqueous mixture be further heated to about 90° C. with stirring to ensure complete hydrolysis of the anhydride to the acid form. Heating is then discontinued although mixing is continued until the batch turns clear with a simultaneous decrease in viscosity (about 65°-75° C.). An aqueous solution of the strontium salt forming compound, or, for example, an aqueous dispersion of particulate strontium carbonate is combined with zinc and iron chloride in the form of a slurry, in an amount sufficient to provide the desired strontium and zinc cationic content desired in the end-product, is separately prepared at ambient temperature and slowly added to the hot polymeric acid solution with continuous vigorous mixing so as to prevent localized precipitation of the cationic polymeric salt. After the zinc, strontium and iron have reacted, an aqueous solution of sodium hydroxide is added slowly, in the amount sufficient to provide the cation sodium content desired in the end-product. After addition is complete, mixing is continued to ensure that all the salt forming compounds are reacted with the copolymer.

Alternatively, an aqueous solution containing the strontium, zinc and iron source is preheated to 70°-80° C. with vigorous stirring to form a homogeneous slurry. The lower alkyl vinyl ether-maleic acid copolymer (I) or its corresponding anhydride is then added to the slurry while further heating to 90° C. and stirring to ensure complete hydrolysis. Alternatively, the AVE/MA copolymer, strontium carbonate, zinc oxide and iron chloride powders are slurried in water at 25° and subsequently heated to 80° C.-90° C. for reaction to occur. Upon completion of this reaction step an aqueous solution of sodium hydroxide is slowly added.

The strontium, and zinc cations in the resultant mixed partial salt of AVE/MA copolymers should be sufficient to give a neutralization ranging from about 0.1% to about 80%, preferably from about 20% to about 65% strontium and from about 0.1% to about 65%, preferably from about 1% to about 40%, more preferably from about 2% to about 20% zinc, resulting in a salt containing free acid in the range of from about 15% to about 40%, preferably from about 20% to about 35%. Sodium is preferably present at a level of from about 0.1% to about 20%.

The reaction batch is then dried such as by shallow drying trays in a convection oven maintained at about 70° C. with hot air circulation to evaporate the water content and recover the polymeric salt product in dry form. Alternatively, the reaction batch is then transferred to drum dryers maintained at 80–100 PSIG with hot steam to evaporate the water content and recover the polymeric salt in the flake form.

The resulting flakes may be subjected to milling and screening to yield the desired physical properties to provide satisfactory denture stabilizing properties.

Said salts are friable so that appropriate particle size and bulk density can be obtained. For best results, drum dried flakes should be milled to a preferred bulk density of about 0.5 to about 1.2 more preferably about 0.6 to about 1.1 and most preferably about 0.7 to about 1.0 grams per cubic centimeter while maintaining a specific surface area of about 0.5 to about 2.5, more preferably about 0.6 to about 2.0, and most preferably about 0.7 to about 1.5 square meters per gram. Ground particles should be capable of passage through a 140- to 200-mesh sieve (U.S.B.S. series) and preferably are less than 0.3 millimeters in their largest dimension. Bulk densities are measured according to ASTM method B-52 (02.05).

The subject strontium, and zinc AVE/MA copolymer salts have exceptional adhesive qualities when contacted with water or saliva such that they are extremely useful as denture adhesive materials in denture stabilizing compositions. For such use the salt in particulate form is preferably characterized by a particle size of at least minus 140-mesh U.S.B.S. sieve; a bulk density greater than 0.3 gram per cubic centimeter and preferably higher then 0.6 gram per cubic centimeter; and a pH between 3 and 8 and preferably between 5 and 7.5, the pH being determined on a one percent by weight dispersion in water.

Each of the subject copolymer salts may be utilized in effective adhesive amounts, preferably at least 25 percent by weight, as the sole adhesive component or as a co-adhesive in joint usage with other active adhesive components in denture stabilizing compositions.

It is preferred that said copolymer salt be used along with a co-adhesive in denture stabilizing compositions.

Preferably, the co-adhesive is a polymeric material selected from the group consisting of natural gums, synthetic polymers, saccharide derivatives, cellulose derivatives, and mixtures thereof. In general, from about 15 to about 70 percent, based on the total weight of the composition, of said mixed calcium/sodium/zinc or strontium salt is present.

Preferred co-adhesives include a water-soluble hydrophilic colloid or polymer having the particular property of swelling upon exposure to moisture to form a mucilaginous mass. Such adhesive materials include both natural gums and synthetic polymeric gums and, among those commonly employed in denture stabilizing compositions and which are also suitable herein co-adhesive action with the subject mixed AVE/MA copolymer salts, there may be mentioned, for example, karaya gum, gelatin, algin, sodium alginate, tragacanth, methylcellulose, acrylamide polymers, ethylene oxide polymers, polyvinylpyrrolidone, cationic polyarylamide polymers and, as the most preferred, sodium carboxymethylcellulose and mixed partial salts of poly(vinyl methylether-maleic acid) copolymer.

Accordingly, a preferred aspect of the subject invention provides a denture stabilizing composition having as a stabilizing component an effective adhesive amount of a mixed partial salt of a lower alkyl vinyl ether-maleic acid copolymer consisting essentially of the repeated structural unit:

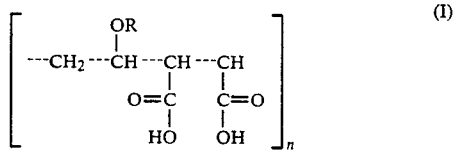

(I)

wherein R represents a $C_1$ to $C_4$ alkyl radical, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salts containing from about 15% to about 40% free acid, and as the cationic salt function:

(a) from about 0.1% to about 80% strontium cations; and (b) from about 0.1% to about 65% zinc cations of the total initial carboxyl groups reacted.

Another preferred aspect of this invention provides a denture stabilizing composition comprising a safe and adhesively effective amount of at least two denture adhesive components, wherein one of said denture adhesive components is the mixed partial salt of a lower alkyl vinyl ether-maleic acid copolymer described above. Preferably the co-adhesive is as described above.

The compositions of the present invention can optionally include from about 0.01% to about 5% of one or more components which provide the user with sensory, including flavor, benefits. Suitable components include menthol, menthyl lactate, peppermint oil, spearmint oil, peppermint oil, leaf alcohol, as well as those paramenthane carboxyamides flavoring agents available from Wilkinson-Sword (such as WS-3) which are described in U.S. Pat. No. 4,136,163 to Watson et al., issued Jan. 23, 1979 which is incorporated by reference herein.

The compositions of the present invention are manufactured in an art-recognized manner known to those skilled in the art, such as in a powder, cream, ointment, liquid, paste, water or film. The compositions of the present invention are preferably manufactured using appropriate micronization such as fluid energy or air jet or hammer milling of drum dried mixed partial salts of AVE/MA copolymer. Suitable examples of such formulations are disclosed in U.S. Pat. No. 4,518,721, issued May 21, 1985 and U.S. Pat. No. 4,514,528, issued Apr. 30, 1985, both to Dhabhar et al. and both of which are hereby incorporated by reference herein.

It is to be recognized that the adhesive salts of the present invention can be used for a wide variety of general adhesive uses including, but not limited to, pharmaceutical uses (e.g., oral drug delivery and topical bandages); and aqueous adhesives (e.g., where adhesiveness in the presence of water is required).

The following non-limiting examples illustrate embodiments of the subject invention wherein both essential and optional ingredients are combined. It is to be understood that these examples are for illustrative purposes only and are not to be construed as limiting the scope of the invention thereto.

EXAMPLE I

Into a reaction vessel equipped with a high speed stirrer and containing 8.6 kg of purified water heated to 85° C., is slowly added 28.4 grams of zinc oxide and 139.7 gm of strontium carbonate. After addition is complete, the temperature of the slurry is kept constant with high speed mixing. While keeping heat and mixing constant add 311 grams of methyl vinyl ether-maleic anhydride copolymer to the reaction vessel containing the alkali dispersion over a 15 minute period. At about 15 minutes the resulting adhesive polymeric dispersion is characterized by an increase in viscosity, and a decrease and stabilization of the reaction pH which is a dispersion of said material in water, said material consisting of mixed partial strontium zinc salt of methyl vinyl ether-maleic acid copolymer. Temperature and mixing remain constant for 60 minutes.

The resultant solution of the strontium zinc salt of methyl vinyl ether-maleic acid (MVE/MA) copolymer is then transferred to shallow stainless steel drying trays and the trays placed in a hot air convection oven at 70° C. for a sufficient time to evaporate the water content (about 16-18 hours). This drying may also be accomplished by drum drying. The thus obtained dried strontium zinc sodium MVE/MA copolymer salt is then ground in a milling apparatus and screened through a 140-mesh sieve and then through a 200 mesh sieve (U.S.B.S. sieve series). The powder would have a bulk density of about 0.6-1.2 gram per cubic centimeter. Analysis of the salt would indicate about 47.5 percent of the carboxyl groups neutralized with strontium and 17.5 percent neutralized with zinc with 35% carboxyl groups remaining unreacted. This particular salt will be referred to hereinafter by the abbreviated term, "47.5% Sr/17.5% Zn partial salt of MVE/MA copolymer".

The product, when used in conjunction with conventional denture adhesives and applied to wet dentures with normal usage, provides denture stabilizing characteristics superior to those obtained by the particular conventional denture adhesive itself.

EXAMPLE II

The procedure of Example I is repeated except that the following amounts of reactants are employed: 309.5 gms of the anhydride copolymer, 8.6 kg purified water; 20.2 gms of zinc oxide; 153.6 gms of strontium carbonate.

The resultant powder would have a bulk density of about 0.6–1.2 grams per cubic centimeter. Analysis of the salt indicates about 45 percent calcium neutralization of the total initial carboxyl groups in the copolymer salt molecule; 9.9 percent neutralization with zinc and 10% neutralization with sodium will be referred to hereinafter by the abbreviated term "52.5%Sn/12.5%Zn sodium partial salt of MVE/MA copolymer".

EXAMPLE III

By following the general procedure of Example I, except that an appropriate amount of zinc oxide is utilized to provide the tabulated zinc substitution, the following strontium/zinc salts of MVE/MA copolymer are obtained:

| Strontium | Zinc |
|---|---|
| 40.4 | 9.6 |
| 43.8 | 16.2 |

Each of the indicated MVE/MA copolymer salts, would have a bulk density for the minus 140-mesh U.S.B.S. sieve powder greater than 0.5 gram per cubic centimeter, and provide markedly beneficial denture stabilizing characteristics. Each of the indicated salts may be abbreviated by the percent of strontium/percent of zinc as done in Examples I and II.

EXAMPLE IV

The MVE/MA copolymeric anhydride-to-acid hydrolysis procedure outlined in Example I is repeated. To a vessel containing 8.5 Kg of purified water heated to 85° C. is added 153 grams of strontium carbonate. With vigorous mixing, 20.1 gm zinc oxide and 6.5 gm of iron chloride is slowly added. After addition is complete, the temperature of the slurry is kept constant mixing, 308 grams of methyl vinyl ether-maleic anhydride copolymer are added to the reaction vessel containing the alkali dispersion over a 20 minute period. This produces a mixed partial strontium, zinc, iron salt of methyl vinyl ether-maleic acid copolymer.

EXAMPLE V

Liquid-type denture stabilizing compositions are prepared by mixing together the following:

|  | % w/w | |
|---|---|---|
|  | A | B |
| Mineral oil, heavy | 44.9 | 43.9 |
| Petrolatum | 3.0 | 5.0 |
| Colloidal silica | 1.5 | 1.0 |
| Sodium carboxymethylcellulose | 35.0 | 20.0 |
| Menthol | 0.1 | 0.1 |
| 47.5% Sr/17.5% Zn/2.5% Fe partial salt of MVE/MA copolymer | 15.5 | 30.0 |
|  | 100.0 | 100.0 |

In use, the above liquid compositions (typically 0.1–1 g) are placed on a premoistened denture, allowed to hydrate briefly, and the denture is inserted in the mouth and pressed into place, all in the manner of denture adhesives well-known in the art.

EXAMPLE VI

A cream-type denture stabilizing composition is prepared by mixing together the following:

|  | % w/w | |
|---|---|---|
|  | A | B |
| Mineral oil, heavy | 24.824 | 24.824 |
| Sodium carboxymethylcellulose | 22.000 | 22.000 |
| Petrolatum | 19.016 | 19.016 |
| Silicon dioxide, colloidal | 1.100 | 1.100 |
| Colorant (oil soluble red color dispersion) | 0.060 | 0.060 |
| 47.5 Sr/17.5 Zn/2.5 Fe partial mixed salt of PVM/MA copolymer | 33.000 | — |
| 47.5 Sr/17.5 Zn partial mixed salt of PVM/MA copolymer | — | 33.000 |

In use, the above compositions (typically 0.1–2 g) are placed on a premoistened denture, and the denture is inserted in the mouth and pressed into place, all in the manner of denture adhesives well-known in the art.

What is claimed is:

1. The mixed partial salt of a lower alkyl vinyl ether-maleic acid copolymer consisting essentially of the repeated structural unit:

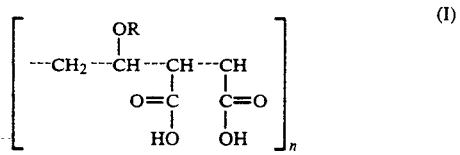

(I)

wherein R represents a $C_1$ to $C_4$ alkyl radical, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salts containing from about 15% to about 40% free acid, and as the cationic salt function:

(a) from about 0.1% to about 80% strontium cations; and (b) from about 0.1% to about 65% zinc cations of the total initial carboxyl groups reacted.

2. The mixed salt of claim 1 wherein R is methyl.

3. The mixed salt of claim 2 wherein said partial salt comprises:

(a) from about 20% to about 65% strontium cations; and (b) from about 1% to about 40% zinc cations of the total initial carboxyl groups reacted and from about 25% to about 35% free acid.

4. The mixed salt of claim 3 which further comprises from about 0.1% to about 25% sodium cations and from about 0.1% to about 10% iron cations, wherein (a) is from about 40% to about 65% strontium cations and wherein (b) is from about 2% to about 20% zinc cations.

5. A denture stabilizing composition having as a stabilizing component an effective adhesive amount of a mixed partial salt of a lower alkyl vinyl ether-maleic acid copolymer consisting essentially of the repeated structural unit:

$$\begin{bmatrix} & \text{OR} & & \\ \text{---CH}_2\text{---CH---CH---CH} & & \\ & \text{O=C} & \text{C=O} & \\ & | & | & \\ & \text{HO} & \text{OH} & \end{bmatrix}_n \quad (I)$$

wherein R represents a $C_1$ to $C_4$ alkyl radical, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salts containing from about 15% to about 40% free acid, and as the cationic salt function:

(a) from about 0.1% to about 80% strontium cations; and (b) from about 0.1% to about 65% zinc cations of the total initial carboxyl groups reacted.

6. The denture stabilizing composition of claim 5 which further comprises from about 0.1% to about 25% sodium cations and from about 0.1% to about 10% iron cations and wherein R is methyl.

7. The denture stabilizing composition of claim 6 wherein said partial salt comprises:

(a) from about 20% to about 65% strontium cations;

(b) from about 1% to about 40% zinc cations; and (c) from about 0.1% to about 5% iron cations of the total initial carboxyl groups reacted and from about 25% to about 35% free acid.

8. The denture stabilizing composition of claim 7 which further comprises from about 5% to about 10% sodium cation and wherein (a) is from about 40% to about 65% strontium cations.

9. A denture stabilizing composition comprising a safe and adhesively effective amount of at least two denture adhesive components, wherein one of said denture adhesive components is the mixed partial salt of a lower alkyl vinyl ether-maleic acid copolymer consisting essentially of the repeated structural unit:

$$\begin{bmatrix} & \text{OR} & & \\ \text{---CH}_2\text{---CH---CH---CH} & & \\ & \text{O=C} & \text{C=O} & \\ & | & | & \\ & \text{HO} & \text{OH} & \end{bmatrix}_n \quad (I)$$

wherein R represents a $C_1$ to $C_4$ alkyl radical, n is an integer greater than one representing the number of repeated occurrences of said structural unit in a molecule of said copolymer and n is large enough to characterize said copolymer as having a specific viscosity larger than 1.2, the specific viscosity being determined in methyl ethyl ketone at 25° C., said partial salts containing from about 15% to about 40% free acid, and as the cationic salt function:

(a) from about 0.1% to about 80% strontium cations; and (b) from about 0.1% to about 65% zinc cations of the total initial carboxyl groups reacted.

10. The denture stabilizing composition of claim 9 wherein R is methyl.

11. The denture stabilizing composition of claim 10 wherein said partial salt comprises:

(a) from about 20% to about 65% strontium cations; and (b) from about 1% to about 40% zinc cations of the total initial carboxyl groups reacted and from about 25% to about 35% free acid.

12. The denture stabilizing composition of claim 11 wherein (a) is from about 40% to about 65% strontium cations and wherein (b) is from about 2% to about 20% zinc cations.

13. The denture stabilizing composition of claim 9 further comprises from about 0.1% to about 10% iron cations and from about 0.1% to about 20% sodium cations.

14. The denture stabilizing composition of claim 12 further comprises from about 0.1% to about 20% sodium cations.

15. The denture stabilizing composition of claim 5 wherein said salt is used along with a co-adhesive, and wherein further said co-adhesive is a polymeric material selected from the group consisting of natural gums, synthetic polymers, saccharide derivatives, cellulose derivatives, and mixtures thereof.

16. The denture stabilizing composition of claim 8 wherein said salt is used along with a co-adhesive, and wherein further said co-adhesive is a polymeric material selected from the group consisting of natural gums, synthetic polymers, saccharide derivatives, cellulose derivatives, and mixtures thereof.

17. The denture stabilizing composition of claim 9 which further comprises from about .01% to about 5.0% of menthol, menthyl lactate, peppermint oil, spearmint oil, peppermint oil, leaf alcohol, and paramenthane carboxyamides, and mixtures thereof.

18. The denture stabilizing composition of claim 14 which further comprises from about .01% to about 5.0% of menthol, menthyl lactate, peppermint oil, spearmint oil, peppermint oil, leaf alcohol, and paramenthane carboxyamides, and mixtures thereof.

* * * * *

UNITED STATES PATENT OFFICE
CERTIFICATE OF CORRECTION

PATENT NO. : 5,304,616
DATED : April 19, 1994
INVENTOR(S) : Jay Rajaiah, et al.

It is certified that error appears in the above-identified patent and that said Letters Patent is hereby corrected as shown below:

Column 9, line 15, "52.5%Sn/12.5%Zn" should be deleted.

Signed and Sealed this

Eighteenth Day of October, 1994

Attest:

BRUCE LEHMAN

Attesting Officer

Commissioner of Patents and Trademarks